(12) United States Patent
Lee

(10) Patent No.: US 7,238,788 B2
(45) Date of Patent: Jul. 3, 2007

(54) ANTIBODIES TO PHOSPHORYLATED TAU, METHODS OF MAKING AND METHODS OF USE

(75) Inventor: Gloria Lee, Iowa City, IA (US)

(73) Assignee: University of Iowa Foundation, Iowa City, IA (US)

( * ) Notice: Subject to any disclaimer, the term of this patent is extended or adjusted under 35 U.S.C. 154(b) by 171 days.

(21) Appl. No.: 11/060,831

(22) Filed: Feb. 18, 2005

(65) Prior Publication Data

US 2005/0196844 A1 Sep. 8, 2005

Related U.S. Application Data

(60) Provisional application No. 60/545,724, filed on Feb. 18, 2004.

(51) Int. Cl.
C07K 16/00 (2006.01)
(52) U.S. Cl. .................. 530/388.1; 435/326; 435/331; 435/7.1
(58) Field of Classification Search ............... None
See application file for complete search history.

(56) References Cited

U.S. PATENT DOCUMENTS

| | | | |
|---|---|---|---|
| 5,492,812 A | 2/1996 | Vooheis | |
| 5,601,985 A | 2/1997 | Trojanowski et al. | |
| 5,843,779 A | 12/1998 | Vandermeeren et al. | |
| 5,861,257 A | 1/1999 | Vandermeeren et al. | |
| 6,008,024 A | 12/1999 | Vandermeeren et al. | |
| 6,010,913 A | 1/2000 | Vandermeeren et al. | |
| 6,121,003 A | 9/2000 | Vanmechelen et al. | |
| 6,232,437 B1 | 5/2001 | Vandermeeren et al. | |
| 6,238,892 B1 | 5/2001 | Mercken et al. | |
| 6,376,205 B1 | 4/2002 | Wischik et al. | |
| 6,417,185 B1 | 7/2002 | Goff et al. | |
| 6,500,674 B1 | 12/2002 | Vandermeeren et al. | |
| 6,512,096 B2 | 1/2003 | Weiner et al. | |
| 6,589,746 B1 | 7/2003 | Zemlan | |
| 6,664,443 B1 | 12/2003 | Hutton et al. | |
| 2002/0001857 A1 | 1/2002 | Vandermeeren et al. | |
| 2002/0019016 A1 | 2/2002 | Vanmechelen et al. | |
| 2002/0168687 A1 | 11/2002 | Wischik et al. | |
| 2002/0188106 A1 | 12/2002 | Mandelkow et al. | |
| 2003/0113896 A1 | 6/2003 | Zinkowski et al. | |
| 2003/0133874 A1 | 7/2003 | Roder | |
| 2003/0138972 A1 | 7/2003 | Vandermeeren et al. | |
| 2003/0143760 A1 | 7/2003 | Vandermeeren et al. | |
| 2003/0165575 A1 | 9/2003 | Iqbal et al. | |
| 2003/0194742 A1 | 10/2003 | Vanmechelen et al. | |

OTHER PUBLICATIONS

Sharma et al. "Spatial Localization of Tyrosine Phosphorylated Tau", Society for Neuroscience Abstract Viewer and Itinerary Planner, (2002) vol. 2002, pp. Abstract No. 592.19, http://sfn. scholarone.com, Meeting Info.: 32nd Annual Meeting of the Society for Neuroscience. Orlando, Flordia, USA, Nov. 2-7, 2002, Society for Neuroscience.*

Lee et al. "Tyrosine Phosphorylated Tau is in Neurofibrillary Tangles" Program No. 19.10. 2003 Society for Neuroscience Abstract Viewer/Itinerary Planner. Online: https://sfn.scholarone. com. Meeting Info.: 33rd Annual Meeting of the Society for Neuroscience. New Orleans, LA, USA, Nov. 8-12, 2003.*

Harlow & Lane. "Antibodies: A Laboratory Manual" (1988) Cold Spring Harbor Laboratory Press, Cold Spring Harbor, NY, pp. 27-34, 141-142, 421, and 423-428.*

Arendt, T., "Alzheimer's Disease as a Loss of Differentiation Control in a Subset of Neurons that Retain Immature Features in the Adult Brain," *Neurobiology of Aging* (2000) 21:783-796.

Bamberger, M.E. et al., "A Cell Surface Receptor Complex for Fibrillar β-Amyloid Mediates Microglial Activation," *J. Neuroscience* (2003) 23:7:2665-2674.

Bondareff, W. et al., "Immunohistochemical Staging of Neurofibrillary Degeneration in Alzheimer's Disease," *J. Neuropath. Exp. Neurol.* (1994) 53:2:158-164.

Bramblett, G.T. et al., "Abnormal Tau Phosphorylation at Ser$^{396}$ In Alzheimer's Disease Recapitulates Development and Contributes to Reduces Microtubule Binding," *Neuron* (1993) 10:1089-1099.

Brandt, R. and Lee, G., "Functional Organization Of Microtubule-Associated Protein Tau." *J. Biol. Chem.* (1993) 268:5:3414-3419.

Carmel et al., "The Structural Basis of Monoclonal Antibody Alz50's Selectivity for Alzheimer's Disease Pathology," *J. Biol. Chem.* (1996) 271:51:32789-32795.

Davis, H.L. et al., "Cpg DNA is a Potent Enhancer of Specific Immunity in Mice Immunized with Recombinant Hepatitis B Surface Antigen," *J. Immunol.* (1998) 160:2:870-876.

Dente, L. et al., "Modified Phage Peptide Libraries as a Tool to Study Specificity of Phosphorylation and Recognition of Tyrosine Containing Peptides," *J. Mol. Biol.* (1997) 269:694-703.

Dickson, D.W. et al., "Immunocytochemistry of Neurofibrillary Tangles with Antibodies to Subregions of Tau Protein: Identification of Hidden and Cleaved Tau Epitopes and a New Phosphorylation Site," *Acta Neuropath.* (1992) 84:596-605.

Digiovanna, M.P., et al., Production of Antibodies that Recognize Specific Tyrosine-Phosphorylated Peptides (2003). *Current Protocols in Immunology*, (1996) 11.6.1-11.6.19.

Endoh, R. et al., "Lack of theCarboxyl Terminal Sequence of Tau in Ghost Tangles of Alzheimer's Disease," *Brain Res.* (1993) 601:164-172.

Garcia-Sierra, F. et al., "Conformational Changes and Truncation of Tau Protein During Tangle Evolution in Alzheimer's Disease," *J. Alzheimers Dis.* (2003) 5:65-77.

Ghoshal, N. et al., "Tau Conformational Changes Correspond to Impairments of Episodic Memory in Mild Cognitive Impairment and Alzheimer's Disease," *Exp. Neurol.* (2002) 177:475-493.

(Continued)

*Primary Examiner*—Long V. Le
*Assistant Examiner*—Christine Foster
(74) *Attorney, Agent, or Firm*—Michael Best & Friedrich LLP

(57) ABSTRACT

Disclosed are antibodies to phosphorylated tau, methods of making and methods of use.

5 Claims, 3 Drawing Sheets

OTHER PUBLICATIONS

Goedert, M. et al., "The Abnormal Phosphorylation of Tau Protein at Ser-202 in Alzheimer Disease Recapitulates Phosphorylation During Development," *Proc. Natl. Acad. Sci. USA* (1993) 90:5066-5070.

Grace, E.A. and Busciglio, J., "Aberrant Activation of Focal Adhesion Proteins Mediates Fibrillar Amyloid Beta-Induced Neuronal Dystrophy," *J. Neurosci.* (2003) 23:2:493-502.

Grant, S.G. et al., "Impaired Long-Term Potentiation, Spatial Learning, and Hippocampal Development in *fyn* Mutant Mice," *Science* (1992) 258:1903-1910.

Hall, G.F. et al., "Human Tau Becomes Phosphorylated and Forms Filamentous Deposits with Overexpressed in Lamprey Central Neurons In Situ," *Proc. Natl. Acad. Sci. USA* (1997) 94:4733-4738.

Herrup, K. and Yang, Y., "Pictures in Molecular Medicine: Contemplating Alzheimer's Disease as Cancer:a Loss of Cell-Cycle Control," *Trends Mol. Med.* (2001) 7:11:527.

Jicha, G.A. et al., "A Conformation- and Phosphorylation-Dependent Antibody Recognizing the Paired Helical Filaments of Alzheimer's Disease," *J. Neurochem.* (1997) 69:5:2087-2095.

Johnson et al., "The τ Protein in Human Cerebrospinal Fluid in Alzheimer's Disease Consists of Proteolytically Derived Fragments," *J. Neurochem.* (1997) 68:1:430-433.

Kanemaru, K. et al., "Fetal-Type Phosphorylation of the τ in Paired Helical Filaments," *J. Neurochem.* (1992) 58:5:1667-1675.

Kim, H. et al., "Evidence for Tau Expression of Cells in Monocyte Lineage and its in Vitro Phosphorylation by V-Fms Kinase," *Oncogene* (1991) 6:1085-1087.

Klein, C. et al., "Process Outgrowth of Oligodendrocytes is Promoted by Interaction of fyn Kinase with the Cytoskeletal Protein Tau," *J. Neurosci.* (2002) 22:3:698-707.

Ksiezak-Reading, H. and Wall, J.S., "Mass and Physical Dimensions of Two Distinct Populations of Paired Helical Filaments," *Neurobiol. Aging* (1994) 15:1:11-19.

Lambert, M.P. et al., "Diffusible, Nonfibrillar Ligands Derived From Abeta 1-42 are Potent Central Nervous System Neurotoxins," *Proc. Natl. Acad. Sci. USA* (1998) 95:6448-6453.

Lee, G., "The Microtubule Binding Domain of Tau Protein," *Neuron* (1989) 2:1615-1624.

Lee, G., "Tau Interacts with Src-Family Non-Receptor Tyrosine Kinases," *J. Cell Sci.* (1998) 111:3167-3177.

Lee, G. et al., "Phosphorylation of tau by Fyn: Implications for Alzheimer's disease," J. Neurosci. (2004) 24(9):2304-2312.

Lee, G. and Rook, S.L., "Expression of Tau Protein in Non-Neuronal Cells: Microtubule Binding and Stabilization," *J. Cell Sci.* (1992) 102:227-237.

Lowell, C.A. and Soriano, P., "Knockouts of Src-Family Kinases: Stiff Bones, Wimpy T Cells and Bad Memories," *Genes Dev.* (1996) 10:1845-1857.

Lu, K.P. et al., "Proline-Directed Phosphorylation and Isomerization in Mitotic Regulation and in Alzheimer's Disease," *Bioessays.* (2003) 25:174-181.

Luo, Y. et al., "Physiologic Levels of β-Amyloid Activate Phosphatidylinositol 3-Kinase with the Involvement of Tyrosine Phosphorylation," *J. Neurochem.* (1996) 67:3:978-987.

Luo, Y.Q. et al., "Physiological Levels of β-Amyloid Increase Tyrosine Phosphorylation and Cytosolic Calcium," *Brain Res.* (1995) 681:65-74.

Mandell, J.W. and Banker, G.A., "A Spatial Gradient of Tau Protein Phosphorylation in Nascent Axons," *J. Neurosci.* (1996) 16:18:5727-5740.

Maness, P.F., "Nonreceptor Protein Tyrosine Kinases Associated with Neuronal Development," *Dev. Neurosci.* (1992) 14:257-270.

Mitchell, T.W. et al., "Novel Method to Quantify Neuropil Threads in Brains from Elders with or without Cognitive Impairment," *J. Histochem. Cytochem.* (2000) 48:12:1627-1637.

Moore, K.J. et al., "A CD36-Initiated Signaling Cascade Mediates Inflammatory Effects of β-Amyloid," *J. Biol. Chem.* (2002) 277:49:47373-47379.

Papasozomenos et al., "Phosphorylation Determines Two Distinct Species of Tau in the Centrall Nervous System," *Cell Motil and the Cytoskel.* (1987) 8:210-226.

Rapoport, M. et al., "Tau is Essential to β-Amyloid-Induced Neurotoxicity," *Proc. Natl. Acad. Sci. USA*, (2002) 99:9:6364-6369.

Sangrajrang, S. et al., "Estramustine Resistance Correlates with Tau Over-Expression in Human Prostatic Carcinoma Cells," *Int. J. Cancer* (1998) 77:626-631.

Sato, N. et al., "Elevated Amyloid β Protein (1-40) Level Induces CREB Phosphorylation at Serine-133 via p44/42 MAP Kinase (Erk 1/2)-Dependent Pathway in Rat Pheochromocytoma PC12 Cells," *Biochem. Biophys. Res. Comm.* (1997) 232:637-642.

Sette, C. et al., "Tr-kit-induced Resumption of the Cell Cycle in Mouse Eggs Requires Activation of a Src-like Kinase," *EMBO J.* (2002) 21:20:5386-5395.

Shapiro, I.P. et al., "Altered Protein Tyrosine Phosphorylation in Alzheimer's Disease," *J. Neurochem.* (1991) 56:4:1154-1162.

Shirazi, S.K. and Wood, J.G., "The Protein Tyrosine Kinase, Fyn, in Alzheimer's Disease Pathology," *Neuroreport* (1993) 4:435-437.

Svensson, H.G. et al., "Protein LA, a Novel Hybrid Protein with Unique Single-Chain Fv Antibody- and Fab-Binding Properties," *Eur. J. Biochem.* (1998) 258:890-896.

Takahashi, M. et al., "Morphological and Biochemical Correlations of Abnormal Tau Filaments in Progressive Supranuclear Palsy," *J. Neuropath. Exp. Neurol.* (2002) 61:1:33-45.

Thomas, et al., "Cellular Functions Regulated by Src Family Kinases," *Ann. Rev. Cell Dev. Biol.* (1997) 13:513-609.

Van Hoesen, et al., "Some Modular Features of Temporal Cortex in Humans as Revealed by Pathological Changes in Alzheimer's Disease," *Cerebral Cortex* (1993) 3:465-475.

Watanabe, A. et al, "In vivo Phosphorylation Sites in Fetal and Adult Rat Tau," *J. Biol. Chem.* (1993) 268:34:25712-25717.

Williamson, R. et al., "Rapid Tyrosine Phosphorylation of Neuronal Proteins Including Tau and Focal Adhesion Kinase in Response to Amyloid-β Peptide Exposure: Involvement of Src Family Protein Kinases," *J. Neurosci.* (2002) 22:1:10-20.

Wood, J.G. and Zinsmeister, P., "Tyrosine phosphorylation systems in Alzheimer's disease pathology," *Neurosci. Lett.* (1991) 121:12-16.

Yang, Y. et al., "DNA Replication Precedes Neuronal Cell Death in Alzheimer's Disease," *J. Neurosci.* (2001) 21:8:2661-2668.

Yasunaga, M. et al., "Involvement of Fyn Tyrosine Kinase in Progression of Cytokinesis of B Lymphocyte Progenitor," *J. Cell Biol.* (1996) 132:91-99.

Zamora-Leon, S.P. et al., Binding of Fyn to MAP-2c Through an SH3 Binding Domain. *J. Biol. Chem.* (2001) 276:43:39950-39958.

Zhang, C. et al., "Focal Adhesion Kinase Expressed by Nerve Cell Lines Shows Increased Tyrosine Phosphorylation in Response to Alzheimer's Aβ Peptide," *J. Biol. Chem.* (1994) 269:41:25247-25250.

\* cited by examiner

ANTIBODIES TO PHOSPHORYLATED TAU, METHODS OF MAKING AND METHODS OF USE

CROSS-REFERENCE TO RELATED APPLICATIONS

This application claims the benefit of U.S. Provisional application No. 60/545,724, filed Feb. 18, 2004.

STATEMENT REGARDING FEDERALLY SPONSORED RESEARCH

This invention was made with Government support under grant AG17753 awarded by the National Institutes of Health. The Government has certain rights in the invention.

INTRODUCTION

A prominent component of the neurofibrillary tangles of Alzheimer's disease (AD) is the microtubule-associated protein tau. A primary characteristic of tau in AD is the presence of several phosphorylated serines and threonines that are less abundant in normal adult brain tau. Abnormal phosphorylation of tau protein is a hallmark characteristic of the neurofibrillary tangles of AD. We previously reported that tau is tyrosine phosphorylated in cells co-transfected with constructs expressing tau and fyn, a src family tyrosine kinase that has a role during the development of the nervous system. (Lee et al., 1998, Journal of Cell Science 111, pages 3167–3177 incorporated herein by reference) Further characterization of these abnormal tau proteins may permit the development of new compositions and methods suitable for detecting abnormal tau in people with AD.

There exists a need in the art for compositions and methods for detecting the presence of abnormal tau proteins in people with AD.

SUMMARY OF THE INVENTION

In one aspect, the present invention provides a purified antibody that selectively binds to a human tau epitope comprising a phosphorylated tyrosine residue corresponding to the tyrosine residue at amino acid position 18 of SEQ ID NO:1.

In another aspect, the present invention provides a cell that produces an antibody deposited as ATCC PTA-6680.

Also provided are methods of making an antibody, comprising immunizing a non-human animal with a tau polypeptide having a sequence comprising a phosphorylated tyrosine residue corresponding to the tyrosine residue at amino acid position 18 of SEQ ID NO:1.

In yet another aspect, the present invention provides a method of making an antibody, comprising culturing a hybridoma cell that produces a monoclonal antibody specific for a tau polypeptide having a phosphorylated tyrosine residue corresponding to the tyrosine residue at amino acid position 18 of SEQ ID NO:1 under suitable conditions that permit production of the monoclonal antibody.

The invention also provides a method of detecting an epitope in a sample, the epitope comprising a phosphorylated tyrosine residue corresponding to the tyrosine residue at amino acid position 18 of SEQ ID NO:1, comprising contacting the sample with an antibody that selectively binds to a human tau epitope comprising a phosphorylated tyrosine residue corresponding to the tyrosine residue at amino acid position 18 of SEQ ID NO:1 and detecting binding of the antibody.

DETAILED DESCRIPTION

Figures 1A, 1B:
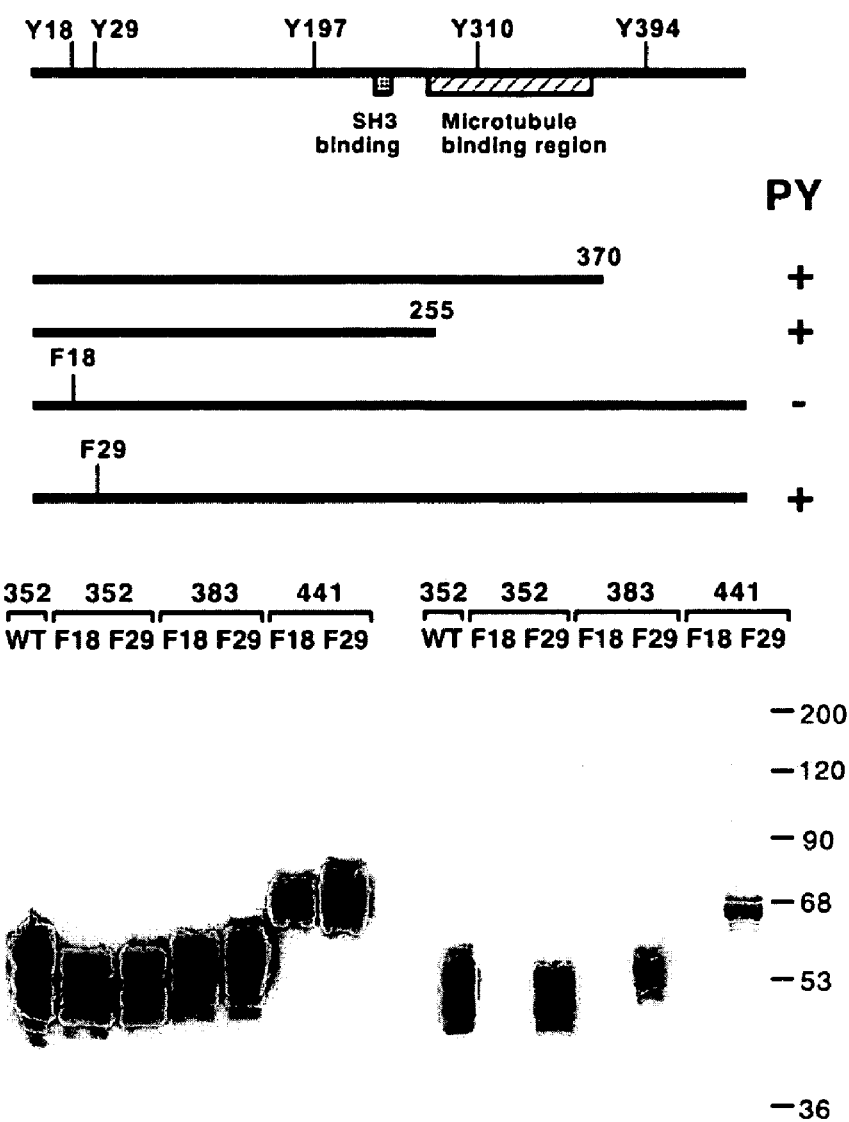
FIG. 1A is a schematic representation showing the relative position of tyrosine residues in native tau and phenylalanine substitutions in mutant tau.
FIG. 1B shows Western blots of native and mutant tau peptides.

As described in detail below, we have now determined that human tau tyr18 is phosphorylated by fyn. Both polyclonal and monoclonal antibodies specific for phospho-tyr18 were developed. Using phospho-tyr18 specific antibodies as probes, we found that phosphorylation of tau at tyr18 occurs in early developmental stages in mouse but is absent in the adult stage. The phospho-tyr18 specific probes also revealed that paired helical filament (PHF) preparations exhibit phospho-tyr18 reactivity that is sensitive to phosphotyrosine specific protein phosphatase treatment. Moreover, immunocytochemical studies indicated that tyrosine phosphorylated tau is present in the neurofibrillary tangles in AD brain. In contrast, neuropil threads and dystrophic neurites did not stain, which indicates that tyrosine phosphorylated tau is distributed in AD brain in a manner dissimilar from other abnormally phosphorylated tau. We also found evidence suggesting that differentially phosphorylated tau exists within degenerating neurons.

As described below in the Examples, polyclonal and monoclonal antibodies were produced against a synthetic 13-amino acid peptide having a sequence corresponding to amino acid residues 12–24 of human tau in which tyrosine 18 is phosphorylated. These antibodies have specificity for tau comprising phosphorylated tyr18, but not for tau having non-phosphorylated tyr18. One such monoclonal antibody, designated 9G3, may be obtained by recovering antibody from the cultured hybridoma, which was deposited with the American Type Culture Collection in Manassas, Va. on Apr. 26, 2005 under the conditions of the Budapest treaty and given Accession No. PTA-6680.

It is specifically envisioned that, using the teachings of the disclosure, one could use any peptide comprising a phosphorylated tyrosine residue corresponding to tyr 18 of the human tau of SEQ ID NO:1 to develop antibodies specific for tau comprising phosphorylated tyr18. For example, one could develop antibodies against a different synthetic peptide or a fragment of a recombinant or naturally occurring tau protein comprising phosphorylated tyr 18. One could use a peptide that is longer or shorter than 13 amino acid residues in length, or a peptide that includes a different portion of the tau sequence than the peptide used in the examples below. For example, it is reasonably expected that, instead of using a peptide having amino acid residues 12–24, one could use, for example, a peptide having residues 10–24 or 14–26, provided that the peptide includes an amino acid residue corresponding to phosphorylated tyr18. Additionally, it is envisioned a polypeptide having a sequence corresponding to, but distinct from, the relevant portion of SEQ ID NO:1 (e.g., residues 10–24, 14–26, or 12–24) could be used to develop antibodies specific for tau comprising phosphorylated tau 18. Such a polypeptide may have one or more minor sequence variations, such as a conservative amino acid substitution. After developing antibodies against the peptide, one could then selectively isolate those antibodies have specificity for tyr18 phosphorylated tau, as described below. An antibody thus produced may be used alone or in conjunction with other antibodies.

Characterization of monoclonal antibodies developed against the 13 amino acid peptide and isolated by affinity binding to the peptide revealed that its binding to tyr18 phosphorylated tau peptide (residues 12–24) was approximately 100,000 times greater than its binding to tau having non-phosphorylated tyr 18 tau peptide. However, the invention is intended to include antibodies having lower specificity as well. Preferably, binding of tyr 18 phosphorylated tau by the antibody will be at least 1,000 times greater than its binding to tau having non-phosphorylated tyr 18.

Antibodies according to the present invention may be used to detect a tau sequence comprising a phosphorylated tyrosine residue corresponding to phosphorylated tyr18 of SEQ ID NO:1 in a sample. Suitable samples for use in the method of the invention include, but are not limited to, cerebrospinal fluid, sectioned brain tissue, or cellular lysates. The sample is contacted with the antibody under conditions that permit specific binding of the antibody to a tau sequence comprising phosphorylated tyr18, and binding is detected. Binding may be detected by any suitable means, many examples of which are well known in the art, including, but not limited to, those methods described herein.

The following non-limiting examples are intended to be purely illustrative.

EXAMPLES

Example 1

COS7 and 3T3 cell Transfections,
Immunoprecipitation and Immunofluorescence

A. Construction of a Tau-GFP Plasmid

Plasmids expressing full length human tau, GFP-tau, fyn, and amino terminal fragments of tau have been previously described, for example in Hall et al., 1997, Proceedings of the National Academy of Sciences USA 94, pages 4733–4738 and Lee and Rook, 1992, Journal of Cell Science 102, pages 227–237, which two documents are herein incorporated by reference. Tau-GFP plasmid was constructed through a modification of the pGFP-C2 vector (Clontech Laboratories Inc., Palo Alto, Calif.) using standard techniques. The moiety encoding GFP was removed by digesting the pGFP-C2 vector with NheI and BglII. The vector ends were made blunt ended and joined by blunt end ligation. The GFP-encoding moiety was amplified by PCR and inserted into a KpnI-Bsp120I digested vector. The modified vector was digested with HindIII, made blunt ended by filling in, and then digested with KpnI. A human tau sequence encoding the 352 residue isoform (Genbank Accession No. AAH00558.1) was amplified by PCR and ligated to the linearized vector by ligating the end corresponding to the amino terminus end to the blunt end of the vector and the end corresponding to the carboxy terminus to the KpnI site at the carboxy end, thus fusing the tau coding sequence in frame with the sequence encoding GFP at the KpnI site. Tyrosine to phenylalanine replacements in tau (Y18F and Y29F) were made using the Stratagene QuikChange Site-Directed Mutagenesis Kit (Stratagene, La Jolla, Calif.).

B. Transfection and of COS Cells and Immunoprecipitation

COS7 cell transfections were performed in 100 mm plates using 5 μg plasmid DNA and LIPOFECTAMINE™ transfection agent (Life Technologies, Inc., Gaithersburg, Md.) according to manufacturer's protocol. For immunoprecipitations, transfected COS7 were lysed and the lysate was subjected to immunoprecipitation using affinity purified anti-tau and Protein A-Sepharose 4B (Amersham Biosciences Corp., Piscataway, N.J.) as previously described in Lee et al., 1998, Journal of Cell Science 111, pages 3167–3177, incorporated herein by reference. After washing, protein-A Sepharose bound proteins were eluted and resolved by 8% SDS-PAGE. For direct analysis of transfected COS cell lysates, cells were harvested in 2× Laemmli sample buffer, boiled, and resolved by 8% SDS-PAGE. Transfer to PVDF membranes (IMMOBILON™-P transfer menbrane, Millipore, Bedford, Mass.) and visualization using enhanced chemiluminescence (ECL) detection was according to manufacturer's instructions (PerkinElmer Life Sciences, Boston, Mass.). Antibodies used for probing blots were tau46.1, tau14, tau1, 5A6 (as described in Johnson et al., 1997, Journal of Neurochemistry 68, pages 430–433), tau5 (as described in Carmel et al., 1996, Journal of Biological Chemistry 271, pages 32789–32795) anti-phosphotyrosine monoclonal 4G10 (Upstate, Charlottesville, Va.), or anti-fyn monoclonal (Transduction Laboratories, Lexington, Ky.). Secondary antibody was sheep anti-mouse Ig, horseradish peroxidase linked F(ab')2 fragment (Amersham Biosciences Corp. Piscataway, N.J.).

C. Transfection and of NIH3T3 Cells and Immunoprecipitation

NIH3T3 cells were seeded onto 12 mm glass coverslips for immunofluorescence analysis. Transfections of seeded cells were performed using LIPOFECTAMINE Plus™ reagent according to manufacturer's protocol. Cells were fixed with 0.3% glutaraldehyde as previously described in Lee and Rook, 1992, Journal of Cell Science 102, pages 227–237, incorporated by reference except with the use of 0.1% instead of 0.5% NP40. Secondary antibodies were obtained from Jackson ImmunoResearch Laboratories, Inc. (West Grove, Pa.) or Molecular Probes (Eugene, Oreg.). To visualize total tau, either an affinity purified anti-tau or the CR antibody preparation (described in Example 2C) were used at 1:1000. Anti-tau antibodies and the CR antibody preparation labeled tau and tau-fyn transfected cells identically. The monoclonal 9G3 (described in Example 2C) was used at approximately 0.5 μg/ml.

Example 2

Preparation of SH-Sy5Y Cells

Figure 3:
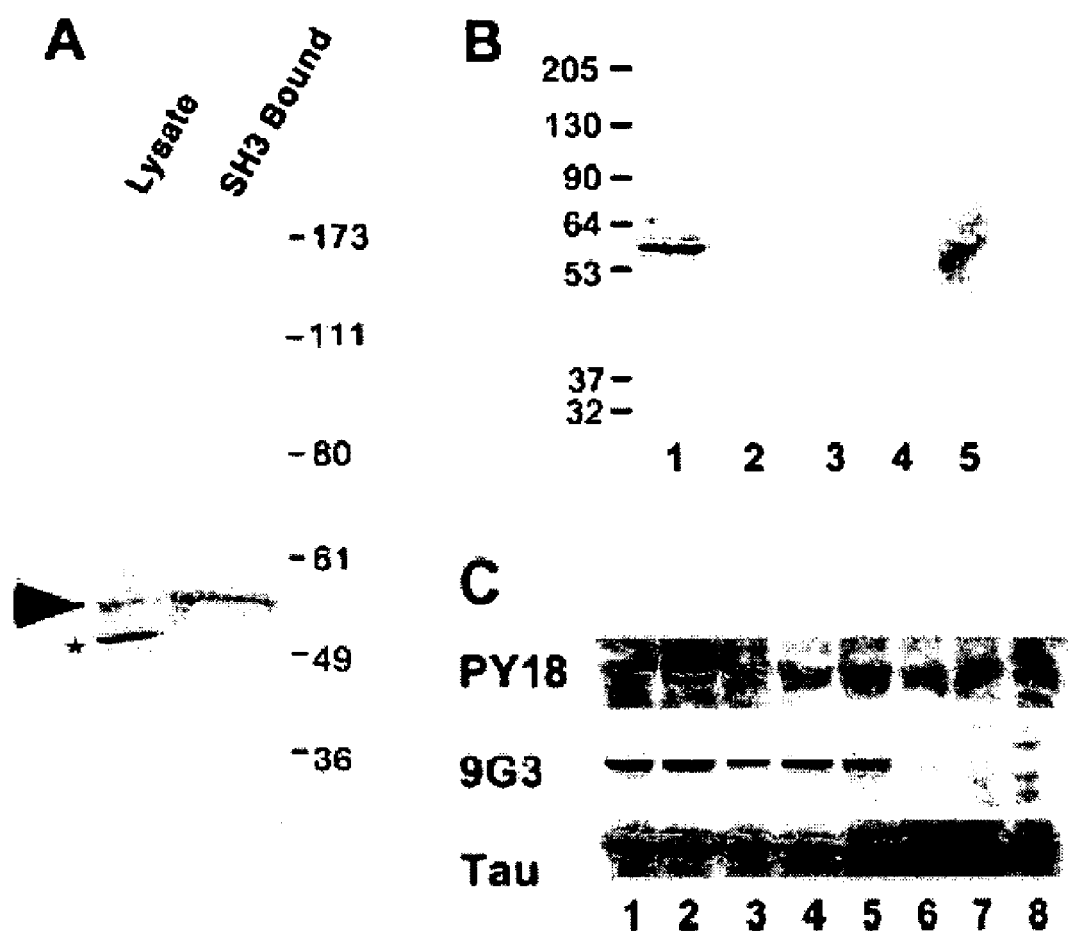
FIG. 3A shows a Western blot of tau from SH-SY5Y cell lysates and GST-fyn bound proteins from SH-SY5Y cells.
FIG. 3B shows a Western blot of tau in SH-SY5Y cell lysates and E. coli tau.
FIG. 3C shows a Western blot of tau from mouse brain lysates.

Growth of SH-SY5Y cells in RPMI with 8% serum conditions and GST-fyn SH3 fusion protein binding assay were performed as previously described Lee et al., 1998, Journal of Cell Science 111, pages 3167–3177, which document is incorporated herein by reference. Briefly, SH-SY5Y cell lysate prepared from a 100 mm plate of cells (about 80% confluency) was reacted with 30 μg purified GST-fyn SH3 fusion protein pre-adsorbed to glutathione Sepharose beads (Amersham Biosciences Corp. Piscataway, N.J.) and incubated for 1 hour at 4° C. The beads were washed in wash buffer (0.5% Triton X-100, 50 mM Tris, pH7.5, 150 mM NaCl). Bound proteins were separated by SDS-PAGE and subjected to immunoblotting. SH-SY5Y cell lysates used in blots displayed in FIG. 3A and 3B contained approximately 1% of the lysate prepared from a 100 mm plate of cells.

Example 3

Preparation of Antibodies

A. Preparation of Anti-PY18 polyclonal serum

Rabbit polyclonal antiserum was prepared against a phosphorylated synthetic tau peptide EDHAGTpYGLGDRK (SEQ ID NO:2) (Research Genetics Inc., Huntsville, Ala.), which corresponds to residues 12–24 of SEQ ID NO:1, the 352 amino acid isoform of tau. To increase specificity, the antiserum was subjected to two steps of affinity purification. The antiserum was first affinity purified using a column containing the phosphorylated peptide. Bound antibodies were eluted and passed through a second column containing non-phosphorylated peptide to adsorb non-phosphorylation specific antibodies. The flowthrough fraction contained antibodies that specifically reacted to the phosphorylated tau epitope. This antibody preparation was named "anti-PY18" and was used at 1:1000 for immunoblotting.

Antibodies adsorbed to the second column were also eluted. These antibodies reacted to the non-phosphorylated tau peptide (residues 12–24 of SEQ ID NO:1) and therefore did not require phosphotyrosine to react. This antibody preparation was named "CR" and was used at 1:1000 for immunocytochemistry.

B. Preparation and Characterization of Monoclonal Antibodies

Monoclonal antibodies were prepared against a phosphorylated synthetic tau peptide EDHAGTpYGLGDRK (SEQ ID NO:2) which corresponds to residues 12–24 of SEQ ID NO:1 (University of Iowa Hybridoma Facility, Iowa City, Iowa). Mice were immunized with the KLH-coupled peptide using CpG 1826 (Hybridon, Milford, Mass.) as adjuvant as described in Davis et al., 1998, Journal Immunology 160, pages 870–876, herein incorporated by reference. Screening of hybridomas by ELISA was performed using biotinylated phosphorylated peptide bound to neutravidin coated microtiter plates as described by Jicha et al., 1997, Journal of Neurochemistry 69, pages 2087–2095, incorporated herein by reference. Peptides were purchased from Multiple Peptide Systems (San Diego, Calif.). Reacting monoclonals were further characterized by ELISA using the non-phosphorylated peptide. Of the phosphorylation specific clones, clone 9G3, whose isotype was IgG2a, was selected for further characterization. Purified 9G3 antibody was obtained by Protein-G HiTrap purification (Amersham Biosciences Corp. Piscataway, N.J.). For blots, 9G3 was used at 0.05–0.2 µg/ml.

The binding kinetics of tyrosine phosphorylated and non-phosphorylated tau peptide (residues 12–24) to monoclonal antibody 9G3 were monitored in real time using surface plasmon resonance ("SPR") with the BIACORE® 3000 instrument (BIAcore AB, Uppsala, Sweden). The sensor chip (CM5, BIAcore AB, Uppsala, Sweden) was activated by 1:1 N-hydroxy succinimide and N-ethyl-N'-(3-dimethilaminopropyl)-carbodiimide hydrochloride (Amersham Biosciences Corp. Piscataway, N.J.) according to manufacturer's protocol. A 75 µl aliquot of recombinant Protein LA (Sigma, St. Louis, Mo.) at a concentration of 100 µg/ml in coupling solution (10 mM sodium acetate; pH 5.0) was immobilized on the activated sensor chip at a flow rate of 5 µl/min using the amine coupling kit (BIAcore AB, Uppsala, Sweden). Protein LA is an immunoglobulin binding protein as described in Svensson et al., 1998, European Journal of Biochemistry 258, pages 890–896, incorporated herein by reference. Excess reactive carboxy methylated dextran on the CM5 sensor chip was then deactivated by 35 µl ethanolamine. All measurements were performed using HBS buffer (10 mM HEPES pH 7.4, 0.15M NaCl, 3 mM EDTA, 0.005% (v/v) Surfactant P20) at 25° C. 30 µg/ml purified 9G3 antibody or the control mouse IgG2a, κ (UPC-10, Sigma, St. Louis, Mo.) was injected (15 µl at 10 µl/min) in sequence with different concentrations of phosphorylated or non-phosphorylated tau peptides (250, 500 and 1000 nM) onto the Protein-LA surface using the "Co-inject" method (BIAcore, 1999). In this method, the injection of a second sample (tau peptide) immediately follows the first (9G3 or IgG2a). Binding responses of the peptides to the control IgG2a surface were subtracted from the binding responses to the 9G3 surface before performing kinetic analysis. Equilibrium association and dissociation rate constants were calculated using the Langmuir (1:1) binding model using the BIAevaluation 3.0 software supplied by the manufacturer.

A control peptide corresponding to a p34cdc2 peptide KVEKIGEGTYGVVY (SEQ ID NO:3) with and without tyrosine phosphorylation at the GTYG motif (Pierce Biotechnology, Rockford, Ill.) was similarly tested for binding to 9G3.

Example 4

In Vitro Phosphorylation of Tau and Microtubule Binding Assays

Tyrosine phosphorylated tau was prepared using fyn or src tyrosine kinase (Upstate Biotechnologies, Inc., Charlottesville, Va.) and *E. coli* synthesized tau (352 residue isoform) purified as previously described in Brandt and Lee, 1993, Journal of Biological Chemistry 268, pages 3414–3419, incorporated herein by reference. One µg *E. coli* synthesized tau was incubated with 4 units of fyn or src at 37° C. for 30 min according to manufacturer's conditions (40 µl final volume). Control kinase reactions omitted either tau or fyn. For analysis of tyrosine phosphorylation, reactions were probed with phosphotyrosine specific antibodies by immunoblotting. For microtubule binding assays, aliquots from the kinase reactions were used without further purification. Taxol stabilized microtubules were prepared from phosphocellulose purified tubulin (Cytoskeleton, Inc., Denver, Colo.). Microtubule binding was performed in a volume of 20 µl by combining 0.25 µg kinased tau and 10 µg taxol stabilized microtubules and incubating at 37° C. for 30 min. The reaction was layered onto a 50% sucrose cushion (160 µl) as described in Lee et al., 1989, Neuron 2, pages 1615–1624, incorporated herein by reference and centrifuged at 100,000×g at room temperature (RT) for 30 min. Both supernatant and pellet were recovered for analysis by Western blotting.

Example 5

Developmental Mouse Brain Samples

Mouse brain lysates were obtained from E18, 1 day, 3 day, 1 week, 2 and 3 weeks, 1 month, 2, 3, 6 and 12 months old ICR mice. 30 µg protein were loaded per lane and immunoblotted with anti-PY18, 9G3, or a cocktail of tau5–5E2 anti-tau monoclonal antibodies. Preparation of the blot was aided by RNWAY Laboratories (Seoul, Korea).

Example 6

Alzheimer's Disease Brain Samples and Immunocytochemistry

Rapid autopsy brains from AD patients were harvested and the temporal lobe was blocked and immersion-fixed in ice cold 4% paraformaldehyde in 0.1 M phosphate buffer (0.1M PBS) for 24–48 hrs. Fixed slab containing the hippocampus and adjacent temporal cortices were cut into 50 µm thick sections on a freezing sliding microtome and stored in cryostorage until processed. Antibodies used were AT8 (Innogenetics, Gent, Belgium;1:1000), 9G3 (25 ng/ml), and CR (1:1000). Sections from five AD brains were examined, with ages ranging from 67 to 87. No qualitative differences in 9G3 labeling were noted between cases.

Free-floating sections were processed for immunohistochemistry as previously described in Van Hoesen and Solodkin, 1993, Cerebral Cortex 3, pages 465–475, incorporated herein by reference, with slight modifications. The sections were quenched with 0.1% $H_2O_2$ in 0.1M PBS containing 0.4% Triton X-100 for 20–30 min. After washing in 0.1M PBS, the sections were blocked with 5% normal goat serum containing 0.4% Triton X-100 in 0.1M PBS for 1 hr at RT. Following the blocking step, the sections were incubated with primary antibody overnight at 4° C. Following washing, sections were incubated with biotinylated goat anti-mouse secondary antibody (1:500, Vector Laboratories, Burlingame, Calif.), washed then incubated with an avidin-biotin peroxidase complex (ABC Elite kit, Vector Laboratories, Burlingame, Calif.) diluted 1:200 in 0.1M PBS containing 0.4% Triton-X 100. After rinsing, for development of a brown color product, 0.03% 3,3'-diaminobenzidine (DAB) in 0.1M PBS containing 0.01% $H_2O_2$ was used for 5–10 min. For development of a black-gray product, 0.03% DAB with 0.25% nickel ammonium sulfate in 0.1M PBS containing 0.01% $H_2O_2$ was used for 5–10 min. Sections incubated in parallel without primary antibody failed to display any specific staining. Sections were rinsed in 0.1M PBS and mounted on gelatin-coated slides, dehydrated through graded ethanol, cleared in xylene, and coverslipped with cytoseal 60 (Richard-Allan Scientific, Kalamazoo, Mich.). For immunofluorescence staining, after primary antibody incubation, sections were incubated with Alexa 488 labeled anti-mouse (Molecular Probes, Inc. Eugene, Oreg.) and Texas red labeled anti-rabbit (Jackson Immunoresearch, West Grove, Pa.). Sections were mounted with Vectashield (Vector Laboratories, Inc., Burlingame, Calif.) and visualized using the 1034 Biorad Confocal system and Nikon E600 microscope. Serial optical sections were collected at 1 or 1.5 µm steps and series of 24–32 sections were collected. Projections described in Example 9C were created using Confocal Assistant (Version 4.02, T. C. Brelje).

Example 7

Preparation of Paired Helical Filaments

PHFs were prepared from temporal or frontal lobes of brains of four AD patients (F82, M86, M78 and M80 y/o, post mortem interval between 3.5–8 hrs, mean: 5.8 hrs) as described earlier in Ksiezak-Reding and Wall, 1994, Neurobiology of Aging 15, pages 11–19, incorporated herein by reference, with minor modifications. Briefly, 10 g tissue were homogenized in 5 volumes of buffer A containing 20 mM Mes/NaOH, pH 6.8, 80 mM NaCl, 1 mM $MgCl_2$, 2 mM EGTA, 0.1 mM EDTA, 10 mM NaF, 1 mM sodium orthovanadate, 0.2 mM PMSF. The homogenate was centrifuged (20 min, 27,000×g) and the pellet was re-homogenized in buffer B, containing 10 mM MES/NaOH, pH 7.4, 0.8M NaCl, 10% sucrose, 1 mM EGTA, 10 mM NaF, 1 mM sodium orthovanadate, 0.2 mM PMSF, and centrifuged as above. The supernatant was incubated with sarcosyl (1% final concentration) for 1 hr at RT or o/n at 4° C. The sarcosyl mixture was then centrifuged (2 hr, 100,000×g). The pellet, which was highly enriched in both dispersed and aggregated PHFs, was resuspended in 10 mM MES/NaOH, pH 7.4 and 1 mM sodium orthovanadate and subjected to discontinuous sucrose gradient as described in Ksiezak-Reding and Wall, 1994, Neurobiology of Aging 15, pages 11–19, incorporated herein by reference, but adding 1 mM sodium orthovanadate to all buffers. In the present studies, both sucrose gradient fractions "A2" and "AL2" were used. A2 contained highly purified and non-aggregated sarcosyl insoluble PHFs. PHFs in the A2 fraction were filamentous (PHF filaments) as examined by electron microscopy and could be resolved into individual PHF tau polypeptides (62–68 kDa) by SDS-PAGE. A2 fraction was used for both Western blot analysis and immunogold EM studies. AL2 contained highly purified and aggregated PHFs that were sarcosyl and SDS insoluble. Clusters and bundles of filaments were detected in this fraction by electron microscopy. AL2 was used for immunogold EM studies.

Immunogold labeling of PHFs was performed as described earlier in Takahashi et al., 2002, Journal of Neuropathology and Experimental Neurology 61, pages 33–45, incorporated herein by reference, using 10-nm colloidal gold particles (Amersham Biosciences Corp., Piscataway, N.J.). Samples were examined using a JEOL 100CX electron microscope.

Example 8

Phosphotyrosine Phosphatase Treatment of Blots

T-cell protein tyrosine phosphatase (New England Biolabs, Beverly, Mass.) was used for phosphotyrosine phosphatase treatment. Blots were incubated with 20 units/ml phosphatase in the reaction buffer (25 mM Tris/HCl, pH 7.0, 50 mM NaCl, 2 mM EDTA, 5 mM dithiothreitol, 0.01 Tween 20 and 1 mg/ml BSA) for 4–24 hrs at 30° C.

Example 9

Development of Antibody Probes Specific for a Tyrosine Phosphorylated in Tau A. Confirmation of the Site of Phosphorylation of Tau by Fyn To determine the site of tyrosine phosphorylation of tau by fyn, we used the COS cell co-transfection system to express fyn and deletion fragments of tau the 352 residue human tau isoform. The five tyrosine residues are represented schematically in FIG. 1A, with numbering according to the 441 adult tau isoform. The immunoprecipitated tau fragments were immunoblotted with an anti-phosphotyrosine monoclonal antibody (4G10), the results of which indicate that the phosphorylation site(s) lay in the amino terminal 255 residues of tau, which contains three of the five tyrosines in tau. To examine which tyrosine residue is phosphorylated, mutations in which tyr18 or tyr29 were replaced with phenylalanine were constructed and tested for tyrosine phosphorylation. The single substitution of tyr18 to phe18 eliminated the tyrosine phosphorylation of tau in the presence of fyn, whereas the mutant tau in which replacement of tyr29 is replaced with phe29 was tyrosine phosphorylated in the presence of fyn. Following co-transfection with fyn into COS7 cells, tau was immunoprecipitated and tested for tyrosine phosphorylation with anti-phosphotyrosine. These data identified tyr18 as a tyrosine phosphorylation site in tau.

B. Detection of Tyrosine Phosphorylation of Tau by anti-PY18 Antibody

To further investigate tyrosine phosphorylated tau, we prepared a rabbit polyclonal antibody, "anti-PY18", as described in Example 2B, against SEQ ID NO:2, a phosphorylated synthetic peptide of tau, corresponding to residues 12–24 of SEQ ID NO:1. The reactivity of affinity purified polyclonal antibody (anti-PY18) was tested on COS7 cells co-transfected with fyn and various tau constructs and comprising tyrosine phosphorylated tau. The schematic drawing of FIG. 1A shows the deletion constructs and point mutants tested for tyrosine phosphorylation (represented as PY in FIG. 1A) in the presence of fyn using co-transfected COS7 cells. All constructs tested were derived from the 352 residue human tau isoform (SEQ ID NO:1), depicted at the top of FIG. 1A with the positions of tyrosines marked (numbering is according to the 441 adult tau isoform; the 441 adult isoform does not contain any additional tyrosines). Two carboxy terminal deletions (lengths 370 and 355) and two point mutants (F18 and F29) were tested: mutations converted either tyr18 to phe18 (shown as F18 in FIGS. 11A and B) or tyr29 to phe29 (shown as F29 in FIGS. 1A and B). Following co-transfection with fyn into COS7 cells, tau was immunoprecipitated and tested for tyrosine phosphorylation with anti-phosphotyrosine. These data identified tyr18 as a tyrosine phosphorylation site in tau. Lysates were probed with anti-PY18 or a cocktail of anti-tau monoclonal antibodies as control. A fyn control blot was also performed, showing that similar amounts of fyn were expressed in each transfection. Mutants of three tau isoforms (amino acid lengths indicated in FIG. 1B as 352, 383 or 441) were tested. The WT of FIG. 1B is wild type tau. Despite the presence of tau in each transfection, F18 mutants did not react with anti-PY18 whereas F29 mutants did (See FIG. 1B). When wild type tau was expressed with fyn, anti-PY18 reacted with proteins in the lysate that correspond to tau as identified by immunoblotting with anti-tau (see FIG. 1B). When tau was mutated in tyr18 and expressed with fyn, anti-PY18 reactivity was lost despite comparable levels of expression relative to the wild type transfection. In contrast, when tyr29 was mutated, anti-PY18 reactivity was retained (see FIG. 1B). These data indicate that anti-PY18 detects tyrosine phosphorylation of tau and are consistent with our mutational analysis identifying tyr18 as a phosphorylated site. In addition, the testing of other tau isoforms (383 and 441 residue isoforms) indicated that alternative splicing of tau did not alter the site modified (see FIG. 1B). The polyclonal preparation (anti-PY18) containing exclusively phosphorylation specific antibodies, may also contain generic phosphotyrosine antibodies that could create background staining of irrelevant tyrosine phosphorylated proteins. Therefore, we chose to use anti-PY 18 primarily on Western blots, because the identity of staining proteins could be supported through other criteria (e.g., molecular weight).

C. Detection of Tyrosine Phosphorylation of Tau by Monoclonal Antibody 9G3

A monoclonal antibody against tyrosine phosphorylated tau residue 18 (9G3) was also prepared (see Example 2C). To obtain direct quantitative data on its specificity, the association and dissociation kinetics of the interaction between 9G3 and tyrosine phosphorylated and non-phosphorylated tau peptides (residues 12–24) were followed by surface plasmon resonance. Different concentrations of each peptide were injected onto a surface coated with 9G3, using a surface coated with purified non-specific mouse IgG2a as control. The kinetic constants are shown in Table 1. The equilibrium association constant (KA=ka/kd) for the association between 9G3 and the phosphorylated tyr18 peptide was $4.04 \times 10^{11}$ $M^{-1}$ while the KA between 9G3 and the non-phosphorylated peptide was $3.33 \times 10^6$ $M^{-1}$. This indicates that 9G3 has a high degree of specificity for the phosphorylated sequence. The dissociation constant (KD=kd/ka) of $2.48 \times 10^{-12}$ M for the interaction between 9G3 and the phosphorylated tyr18 peptide indicates a high affinity of the antibody for the phosphorylated residue. As further characterization of the specificity of the antibody, we tested 9G3 for reactivity against a control tyrosine phosphorylated p34cdc2 peptide that contains a known fyn phosphorylation site. The surface plasmon resonance response was below baseline, precluding any kinetic analysis. This indicates that the reactivity of 9G3 against generic phosphotyrosine was extremely low.

TABLE 1

Kinetic constants for the interaction between 9G3 and tau peptide (residues 12–24), obtained by the 1:1 Langmuir binding model.

| | $k_a$ ($M^{-1} s^{-1}$) | $k_d$ ($s^{-1}$) | $K_A$ ($M^{-1}$) | $K_D$ (M) |
|---|---|---|---|---|
| 9G3 and tau non-phospho peptide | $30.7 \pm 0.2$ | $9.22 \pm 0.74 \times 10^{-6}$ | $3.33 \pm 0.2 \times 10^6$ | $3.0 \pm 0.27 \times 10^{-7}$ |
| 9G3 and tau phospho-peptide | $9.26 \pm 0.8 \times 10^5$ | $2.29 \pm 0.1 \times 10^{-6}$ | $4.04 \pm 0.3 \times 10^{11}$ | $2.48 \pm 0.18 \times 10^{12}$ |

The ability of 9G3 to differentiate between phosphorylated and non-phosphorylated tau in immunocytochemistry protocols was demonstrated by immunofluorescence staining of 3T3 cells expressing tau only, or tau and fyn. Cells were fixed and double stained with CR for total tau and 9G3 for tyrosine phosphorylated tau. 3T3 cells transfected with fyn and GFP-tau or fyn and tau-GFP were fixed and stained with 9G3. The presence of fyn is required for 9G3 reactivity. The 9G3 staining pattern does not correspond to the total tau pattern, indicating that in staining fixed cells, 9G3 recognizes a fraction of the total tau. This is consistent with our finding that the efficiency of tyrosine phosphorylation of tau in fyn-tau co-transfected cells is less than 100%. Tyrosine phosphorylated tau appeared as punctate staining seen along microtubules, suggesting that it is capable of associating with microtubules in cells. When a GFP-tau construct was used in the co-transfection, 9G3 reactivity was absent. As GFP-tau contains GFP fused at the amino terminus of tau in close proximity to tyr18, we surmised that the GFP fusion might either interfere with the phosphorylation of tyr18 or with the reactivity of the antibody. In fact, when we employed a tau fusion protein with GFP fused to the carboxy terminus of tau (tau-GFP), co-expression of tau-GFP with fyn restored 9G3 reactivity. To determine if GFP-tau was, in fact, tyrosine phosphorylated on tyr18, we assayed the phosphorylation by Western blotting using anti-PY18. We found that when GFP-tau and tau-GFP were expressed at comparable levels in the presence of fyn, both proteins were similarly phosphorylated. Therefore, the accessibility of phospho-tyr18 to 9G3 in fixed cells was affected by the amino terminal GFP fusion.

Our hypothesis that tyr18 is phosphorylated in PHF is strongly supported by the reactivity of monoclonal antibody 9G3 to fixed AD tissue. The surface plasmon resonance data for this monoclonal suggests that its affinity for the phosphorylated tau sequence is about 105 times higher than its affinity for the non-phosphorylated sequence with the KD of the antibody being in the picomolar range. We also showed that 9G3 does not react to a tyrosine phosphorylated peptide containing the fyn substrate sequence (ETYG), underscoring its specificity for the sequences around tyr18.

The monoclonal reagent (9G3), though tau specific, had some affinity for non-phosphorylated tau that could create phosphorylation independent staining in the presence of high levels of tau. 9G3 may be particularly useful on tissue and fixed cell samples, in which the amount of tau in single cells would be low relative that levels involved in biochemical protocols involving tau overexpression.

Example 10

Phosphorylation of Tyr18 by Fyn and its Impact on Microtubule Binding

The availability of a phosphorylation specific antibody allowed us to demonstrate the phosphorylation of tau by fyn on tyr18 in vitro.

Figure 2A:
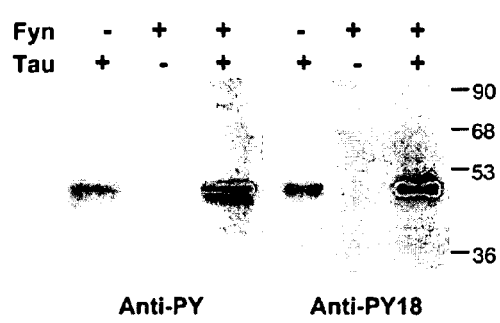
FIG. 2A shows Western blots of tau and tyrosine phosphorylated tau.
Figure 2B:
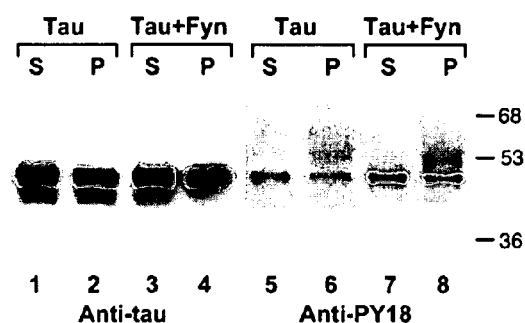
FIG. 2B shows Western blots of tau and tyrosine phosphorylated tau after incubation with microtubules.

In vitro kinase reactions were performed with E. coli synthesized tau and fyn as described in Example 3. Reactions were probed with either anti-phosphotyrosine (4G10) or anti-PY18. Note that fyn kinased tyr18 in vitro as evidenced by the acquisition of anti-PY18 and anti-PY reactivity after incubation of tau with fyn. E. coli synthesized tau, incubated with or without kinase, was incubated with taxol stabilized microtubules as described in Example 3. The distribution of tyrosine phosphorylated tau between the supernatant and pellet was similar to that of non-phosphorylated tau. Following incubation of E. coli synthesized tau with fyn, tau became reactive to both anti-PY18 and 4G10 (FIG. 2A). Identical results were observed for src. This confirmed that tau is a substrate for src family non-receptor tyrosine kinases. In vitro tyrosine phosphorylated tau was then tested for its ability to bind to taxol stabilized microtubules, using non-phosphorylated tau as a control. Following the incubation of tau with microtubules, centrifugation was used to separate microtubule bound tau (pellet) from unbound tau (supernatant). The supernatants containing unbound tau (S, odd lanes in FIG. 2B) and the pellets containing microtubule bound tau (P, even lanes in FIG. 2B) were examined for the presence of tau. Tau in lanes 1, 2, 5, and 6 of FIG. 2B was from a control kinase reaction without fyn whereas tau in lanes 3, 4, 7, and 8 of FIG. 2.B was from a fyn kinase reaction. Pellets and supernatants were probed by both anti-tau and anti-PY18 (FIG. 2B). Non-phosphorylated tau bound to microtubules with almost 50% efficiency (lanes 1 and 2 of FIG. 2B) while tau from the kinase reaction appeared to have a similar binding efficiency of about 50% (lanes 3 and 4 of FIG. 2B), with tau being almost equally distributed between the supernatant and pellet. Because the stoichiometry of phosphate incorporation in the in vitro kinase reaction was not determined, we probed the same fractions with anti-PY18 and found that tyrosine phosphorylated tau was similarly distributed between bound and unbound fractions (lanes 7 and 8 of FIG. 2B). This suggested that tyrosine phosphorylation of tau by fyn did not largely alter the microtubule binding behavior of tau. This is consistent with the data from transfected cells showing the association of tyrosine phosphorylated tau with microtubules.

Example 11

Presence of Phospho-tyr18 in Neuronal Cells and in Degenerating Neurons

A. Presence of Phospho-tyr18 in Neuronal Cells

To determine if tau tyr18 was phosphorylated in neuronal cells, anti-PY18 was used to probe lysates from human neuroblastoma (SH-SY5Y) cells. [0071] (A). SH-SY5Y cell lysate (left lane of FIG. 3A) and GST-fyn SH3 bound proteins from SH-SY5Y cells (right lane of FIG. 3A) were immunoblotted with anti-PY18. Two reactive species were revealed (FIG. 3A), with the upper species (indicated by the arrowhead) corresponding to endogenous tau in mobility. The lower species (indicated by the asterisk) was a cross-reactive non-tau protein with a mobility corresponding to that of tubulin. To confirm the identity of the upper species as tau, fyn-SH3 binding proteins were isolated from SH-SY5Y lysates using GST fusion protein mediated binding assays. Our previous studies had shown that SH-SY5Y tau binds to GST-fyn-SH3. Using anti-PY18 to probe proteins binding to fyn SH3 confirmed that the upper band is tau (FIG. 3A); unlike tau, the cross-reactive protein did not bind to fyn SH3. The monoclonal 9G3 was also used to probe a lysate from SH-SY5Y cells. SH-SY5Y cell lysate (lane 1 of FIG. 3B) and 25, 100, 400, and 1000 ng E. coli tau (lanes 2, 3, 4, and 5 respectively of FIG. 3B) were immunoblotted with monoclonal antibody 9G3. The 25–1000 ng of E. coli tau were probed in parallel as a specificity control. The monoclonal 9G3 reacted to a single species in the cell lysate without reacting to non-phosphorylated tau under the same conditions (FIG. 3B), thus confirming the phosphorylation of tau at residue 18 in neuronal cells. Mouse brain (30 μg tissue lysate per lane) was probed with anti-PY18, 9G3, or a cocktail of tau monoclonal antibodies 5E2 and tau5. Lysates, depicted in lanes 1–8 of FIG. 3C were from 1) E18, 2) 1 day post-natal, 3) 3 day post-natal, 4) 1 week old, 5) 2 weeks old, 6) 3 weeks old, 7) 1 month old, and 8) 1 year old mouse. Probing of lysates from 2, 3, and 6 months old mice showed data similar to that of the 1 month old mouse.

B. Presence of Phospho-Tyr18 During Brain Development

The tyrosine phosphorylation of tau during brain development was examined in mouse by immunoblotting using both anti-PY18 and 9G3. The results indicated that tyrosine phosphorylated tau was most abundant at E18 and 1D post-natal (FIG. 4C). Though still present at 3D and 1 week post-natal, it no longer appeared after 2 weeks (oldest time point examined was 1 year). This pattern of expression suggests that tyrosine phosphorylated tau has a role in early neuronal development and is consistent with fyn's role in neuronal development as described in Grant et al., 1992, Science 258, pages 1903–1910, herein incorporated by reference.

Interestingly, several serines and threonines that are highly phosphorylated in rat fetal tau, described in Watanabe et al., 1993, Journal Biological Chemistry 268, pages 25712–25717, herein incorporated by reference, are also down regulated in adult. In addition, several of these sites are also phosphorylated in human fetal tau and correspond to sequences that are highly phosphorylated in the neurofibrillary tangles of AD brain (e.g., the Ser198–Ser 208 region that reacts with AT8 and the ser396–ser404 region that reacts with PHF-1) (described in Bramblett et al., 1993, Neuron 10, pages 1089–1099; Goedert et al., 1993, Proceedings of the National Academy of Sciences 90, pages 5066–5070; Kanemaru et al., 1992, Journal of Neurochemistry 58, pages 1667–1675, which three documents are herein incorporated by reference). Because phosphorylated tyr18 has a similar developmental profile, we tested AD brain tissue for the presence of phosphorylated tyr18.

C. Presence of Phospho-Tyr18 in Degenerating Neurons

Temporal cortex sections from AD brain containing the entorhinal and hippocampal formation were probed with 9G3. Sections were labeled with either 9G3 or AT8 followed by development using DAB and nickel ammonium sulfate (see Example 5 for details). The staining pattern was compared to that of a proven PHF antibody, AT8. We found that 9G3 labeled neurofibrillary tangle-bearing neurons in the entorhinal layer II islands in a manner indistinguishable from AT8. In contrast to AT8 however, 9G3 did not label neuropil threads and dystrophic neurites. This suggested that phosphotyrosine residue 18 is present in only some PHF. This was further illustrated by immunofluorescent double labeling of brain sections using 9G3 and CR, an antibody affinity purified using the non-phosphorylated peptide containing tyr18 (see Example 2C). Single optical sections of degenerating hippocampal neurons from the entorhinal cortex of AD brains were double labeled with CR and 9G3 and visualized by double immunofluorescence confocal microscopy. CR labeling was detected by texas red and 9G3 by Alexa 488 (see Example 5 for detection details). The projections were created from series of 24 to 32 serial sections collected at either 1 or 1.5 μm steps. Confocal microscopy showed that CR labeling did not necessarily coincide with 9G3 labeling, suggesting that while tyrosine phosphorylated tau existed in neurofibrillary tangles, not all of the neurofibrillary tangles had phosphotyrosine. Close inspection of several series of 9G3 and CR double labeled sections revealed that the intensity of 9G3 labeling often "peaked" at a different section relative to the CR labeling. Projections integrating the signals from series of z-sections suggested that 9G3 labeling was less abundant than CR in distal regions. Therefore, the staining patterns of the two probes are distinct, suggesting that there is spatial specificity of tyrosine phosphorylation within the neuron. These data further support the specificity of 9G3 and indicate that tau phosphorylated at residue 18 is present in neurofibrillary tangles in degenerating neurons.

Example 12

Biochemical Detection of Tyrosine Phosphorylated Tau in PHF Tau Polypeptides

To demonstrate on a biochemical level that PHF tau polypeptides contained tyrosine phosphorylated tau, PHF preparations were probed with either 4G10 or anti-PY18 on immunoblots. 2 μg PHFs were probed with anti-tau or anti-phosphotyrosine mAb4G10. 0.6 μg PHFs were probed with anti-tau or anti-PY18. Both tyrosine phosphorylation specific probes (anti-phosphotyrosine mAb4G10 and anti-PY18) labeled PHF tau polypeptides. (FIG. 7A, lanes 2 and 4); we were able to detect 4G10 or anti-PY18 reactivity was detected in 3 different PHF preparations tested. In addition, 0.6 μg PHFs were probed with anti-PY18 after the membrane was incubated with phospho-tyrosine specific protein phosphatase. Mock incubation without phosphatase was similarly probed. In additionT, the reactivity of anti-PY18 decreased to 61+8% (SD, n=3) after treatment with a phosphotyrosine phosphatase (FIG. 7A, lanes 5 and 6). As further confirmation, PHFs were labeled with PY20 and 10 nm gold labeled anti-mouse. Control labeling of the preparation was by 46.1. PHF filaments, examined by electron microscopy in four AD brains with short post-mortem interval (mean<6 hrs), showed immunogold labeling with anti-phosphotyrosine antibody (FIG. 7B). Both non-aggregated (A2) and aggregated (AL2) insoluble filaments showed labeling.

The invention claimed is:

1. An antibody produced by hybridoma 9G3, ATCC accession number PTA-6680.

2. A cell of hybridoma 9G3, ATCC accession number PTA-6680.

3. A method of detecting binding of an antibody to phosphorylated tau, comprising:

contacting the sample with the antibody of claim 1; and detecting binding of the antibody.

4. The method of claim 3, wherein the sample is sectioned brain tissue.

5. The method of claim 3, wherein the sample is cerebrospinal fluid.

* * * * *

SEQUENCE LISTING

```
<160> NUMBER OF SEQ ID NOS: 3

<210> SEQ ID NO 1
<211> LENGTH: 352
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60
```

```
Thr Gln Ala Arg Met Val Ser Lys Ser Lys Asp Gly Thr Gly Ser Asp
 65                  70                  75                  80

Asp Lys Lys Ala Lys Gly Ala Asp Gly Lys Thr Lys Ile Ala Thr Pro
                 85                  90                  95

Arg Gly Ala Ala Pro Pro Gly Gln Lys Gly Gln Ala Asn Ala Thr Arg
            100                 105                 110

Ile Pro Ala Lys Thr Pro Ala Pro Lys Thr Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
                180                 185                 190

Pro Asp Leu Lys Asn Val Lys Ser Lys Ile Gly Ser Thr Glu Asn Leu
            195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
                260                 265                 270

His Val Pro Gly Gly Gly Asn Lys Lys Ile Glu Thr His Lys Leu Thr
            275                 280                 285

Phe Arg Glu Asn Ala Lys Ala Lys Thr Asp His Gly Ala Glu Ile Val
    290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 2
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 2

Glu Asp His Ala Gly Thr Tyr Gly Leu Gly Asp Arg Lys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic polypeptide
```

```
<400> SEQUENCE: 3

Lys Val Glu Lys Ile Gly Glu Gly Thr Tyr Gly Val Val Tyr
1               5                   10
```